United States Patent [19]

Van Gestel et al.

[11] Patent Number: 5,013,746

[45] Date of Patent: May 7, 1991

[54] IMAZALIL CONTAINING SYNERGISTIC COMPOSITIONS

[75] Inventors: Jozef F. E. Van Gestel, Vosselaar; Jan R. Nys, Antwerp; Paul F. M. Ruelens, Herk-de-Stad, all of Belgium

[73] Assignee: Janssen Pharmaceutica N.V., Beerse, Belgium

[21] Appl. No.: 355,023

[22] Filed: Apr. 7, 1989

Related U.S. Application Data

[63] Continuation-in-part of Ser. No. 284,761, Dec. 12, 1988, abandoned, which is a continuation of Ser. No. 179,451, Apr. 8, 1988, abandoned.

[51] Int. Cl.$^5$ .................... A01N 43/50; A01N 43/64; A01N 43/78
[52] U.S. Cl. .................... 514/365; 514/383; 514/399
[58] Field of Search .................... 514/365, 383, 399

[56] References Cited

U.S. PATENT DOCUMENTS

| | | | |
|---|---|---|---|
| 3,017,415 | 1/1962 | Sarett et al. | 260/302 |
| 3,658,813 | 4/1972 | Godefroi et al. | 260/240 K |
| 4,079,062 | 3/1978 | Van Reet et al. | 260/308 R |
| 4,507,140 | 3/1985 | Sugavanam | 71/76 |
| 4,636,247 | 1/1987 | Clough et al. | 71/92 |

FOREIGN PATENT DOCUMENTS

| | | | |
|---|---|---|---|
| 0209234 | 1/1987 | European Pat. Off. | 548/341 |
| 2823818 | 12/1979 | Fed. Rep. of Germany | 548/127 |
| 2922292 | 2/1980 | Fed. Rep. of Germany | 514/184 |
| 2916853 | 11/1980 | Fed. Rep. of Germany | 548/262 |

OTHER PUBLICATIONS

Hide et al., Control of Potato Diseases with Fungicides Applied to Seed Tubers, Tests of Agorchemicals and Cultivars 8 (1987), Ann. Appl. Biol. 110 (supplement), pp. 72–73.

Hide et al., Chem. Abst. 107:54035m (1987).

*Primary Examiner*—Dale R. Ore
*Attorney, Agent, or Firm*—Charles J. Metz

[57] ABSTRACT

Synergistic antifungal compositions containing imazalil and propiconazole. Methods of treating plants comprising the administration of imazalil and propiconazole.

11 Claims, No Drawings

IMAZALIL CONTAINING SYNERGISTIC COMPOSITIONS

CROSS REFERENCE TO RELATED APPLICATIONS

This is a continuation-in-part of our copending application Ser. No. 284,761, filed Dec. 12, 1988 which in turn is a continuation of Ser. No. 179,451, filed Apr. 15, 1988 both now abandoned.

BACKGROUND OF THE INVENTION

Various classes of compounds are known as antimicrobial and in particular antifungal compounds. Among these classes, the group of imidazole and triazole derivatives is of particular interest and several of such compounds are now widely used as antimicrobials and in particular as antifungals. Another such class of antifungal compounds comprises the thiazolyl substituted benzimidazoles.

Further, there are known fungicidal combinations comprising two or more such fungicidally active compounds. DE-A-2816853 describes a combination of fenfuran, thiabendazole and imazalil for treating cereal grains. DE-A-2922292 describes combinations of a furan-3-carboxamide, imazalil and/or thiabendazole. DE-A-2823818 describes mixtures of 2,4,5-trimethyl-N-phenyl-3-furancarboxamide with imazalil and/or thiabendazole.

It now has been found that the compounds imazalil and propiconazole act synergistically.

SUMMARY OF THE INVENTION

The present invention is concerned with synergistic mixtures or compositions containing an antifungally effective amount of the compound imazalil or a salt form thereof and propiconazole or a salt form thereof.

DESCRIPTION OF THE PREFERRED EMBODIMENTS

Imazalil as mentioned hereinabove is the generic name of the compound 1-[2-(2,4-dichlorophenyl)-2-(2-propenyloxy)ethyl]-1e,uns/H/ -imidazole, which compound may be represented by the formula

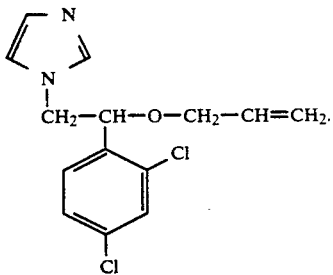

(I)

This compound, its synthesis as well as its antifungal properties are described in U.S. Pat. No. 3,658,813, incorporated herein by reference.

Propiconazole as mentioned hereinabove is the generic name of the compound 1-[[2-(2,4-dichlorophenyl)-4-propyl-1,3-dioxolan-2yl]methyl]-1e,uns/H/ -1,2,4-triazole, which compound may be represented by the formula

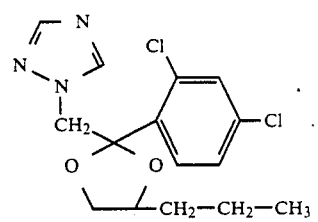

(II)

This compound, its synthesis as well as its antifungal properties are described in U.S. Pat. No. 4,079,062, incorporated herein by reference.

The active ingredients for use in the mixtures or compositions according to the present invention may be used as stereochemical mixtures or as pure stereoisomers. In particular, propiconazole may occur as 2,4-cis or 2,4-trans isomers. The 2,4-cis isomer is preferably used in the compositions of the present invention. Or use may be made of stereochemical mixtures containing predominantly (over 50%) of the cis isomer.

The active ingredients (I) and (II)) may be present in base or in salt form, the latter being obtained by reaction of the base form with an appropriate acid. Appropriate acids comprise, for example, inorganic acids, such as the hydrohalic acids, i.e. hydrofluoric, hydrochloric, hydrobromic and hydroiodic, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

The term salt form also comprises metal complexes which the basic components (I) or (II) may form. One of the components may occur as a complex and the other not; or both or all three components may occur as a complex; or two or three of the active ingredients may occur in a mixed complex. Metal complexes as mentioned above consist of a complex formed between one or more molecules of the active ingredient and one or more organic or inorganic metal salt or salts. Examples of said organic or inorganic salts comprise the halogenides, nitrates sulfates, phosphatse, acetates, trifluoroacetates, trichloroacetates, propionates, tartrates, sulfonates, e.g. methylsulfonates, 4-methylphenylsulfonates, salicylates, benzoates and the like of the metals of the second main group of the periodical system e.g. the magnesium or calcium salts, of the third or fourth main group, e.g. aluminium, tin, lead as well as the first to the eighth transition groups of the periodical system such as, for example, chromium, manganese, iron, cobalt, nickel, copper, zinc and the like. Preferred are the metals pertaining to the transition elements of the fourth period. The metals may be present in each of their possible valences. The complexes can be mono- or polynuclear, they may contain one or more parts of the organic molecule as ligands.

The ratio between the active ingredients of formula (I) and (I) may vary within relatively broad ranges and will be dependent on the application aimed at, however said ratio will be so that both active ingredients act synergistically. Particularly, it is contemplated that the weight ratio between the active ingredients (I) and (II) (imazalil: propiconazole) may be situated between 50:1 and 1:50, more particularly between 20:1 and 1:20. Preferably said ratio is between 10:1 and 1:10 more preferably between 5:1 and 1:5, or between 1:5 and 1:1, or between 1:2 and 1:1.

The quantity of each of the active ingredients in the compositions according to the present invention will be so that a synergistic anti-fungal effect is obtained. In particular, it is contemplated that in the compositions to be used directly to the plants or the loci thereof, the concentration of imazalil, taken as base equivalent, will be from 100 to 5000 ppm, in particular from 200 to 4000 ppm or from 200 to 2000 ppm, more in particular from 400 to 600 ppm; the concentration of propiconazole taken as base equivalent is contemplated to be in the range from 200 to 10000 ppm, in particular from 400 to 8000 ppm or from 400 to 4000 ppm, more in particular from 800 to 1200 ppm. However, when the active ingredients are formulated as waxes for use as a cover or coating of e.g. fruits, in particular citrus fruits, the concentration of imazalil taken as base equivalent, will preferably be in the range of 500–8000 ppm, in particular of 500 to 4000 ppm, or of 500 to 2000 ppm or of 750 to 1250 ppm; the concentration of propionazole in such waxes, taken as base equivalent, will be in the range of 1000 to 10000 ppm, in particular of 1000 to 8000 ppm or of 1000 to 4000 ppm, or of 1500 to 2500 ppm. The said compositions to be used directly, in many instances, are obtained from concentrates upon dilution with aqueous or organic media, such concentrates being intended to be covered by the term composition as used in the definitions of the present invention.

The synergistic mixtures of the present invention are active against a broad range of fungi. As examples of such fungi there may be named Ascomycetes (e.g. Venturia, Podosphaera, Erysiphe, Monilinia, Uncinula); Basidiomycetes(e.g. Hemileia, Rhizoctonia, Puccinia); Fungi imperfecti(e.g. Botrytis, Helminthosporium, Rhynchosphorium, Fusarium, Septoria, Cercospora, Alternaria, Pyricularia, Penicillium, Geotrichum).

The synergistic mixtures according to the present invention possess advantageous curative, preventive and systemic fungicidal activity to protect plants, in particular culture plants. The present mixtures can be used to protect plants or parts of plants, e.g. fruits, blossoms, flowers, foliage, stems, roots, tubers of plants or culture plants infected, harmed or destroyed by microorganisms, whereby later-growing parts of plants are protected against such microorganisms.

The mixtures according to the present invention shown systemic activity. They can further be used in seed disinfection (fruits, tubers, cereal grains) and to treat plant cuttings as well as to combat phytopathogenous fungi occurring in the soil. The mixtures of the present invention are particularly attractive due to their good plant tolerance and lack of environmental problems.

As examples of the wide variety of culture plants in which the combinations of active ingredients according to the present invention can be used, there may be named for example cereals, e.g. wheat, barley, rye, oats, rice, sorghum and the like; beets, e.g. sugar beet and fodder beet; pome and stone fruits and berries, e.g. applies, pears, plums, peaches, almonds, cherries, strawberries, raspberries and blackberries; leguminous plants, e.g. beans, lentils, peas, soy beans; oleaginous plants, e.g. rape, mustard, poppy, olive, sunflower, coconut, castor-oil plant, cocoa, ground-nuts; cucurbitaceae, e.g. pumpkins, gherkins, melons, cucumbers, squashes; fibrous plants, e.g. cotton, flax, hemp, jute; citrus fruits, e.g. orange, lemon, grapefuit, mandarin; vegetables, e.g. spinach, lettuce, asparagus, brassicaceae such as cabbages and turnips, carrots, onions, tomatoes, potatoes, hot and sweet peppers; laurel-like plants, e.g. avocado, cinnamon, camphor tree; or plants such as maize, tobacco, nuts, coffee, sugar-cane, tea, vines, hops, bananas, rubber plants, as well as ornamental plants, e.g. flowers, shrubs, deciduous trees and evergreen trees such as conifers. This enumeration of culture plants is given with the purpose of illustrating the invention and not to delimiting it thereto.

The combinations of active ingredients of formulae (I) and (II) are preferably applied as compositions. The active ingredients of formula (I) and those of formula (II) can be applied to the plants or to the loci thereof simultaneously, or can also be administered consecutively within a time period selected so that both active ingredients are allowed to act synergistically, e.g. within 24 hours. In such applications, the active ingredients are used optionally together with adjuvants conventionally employed in the art of formulation such as carriers, surfactants or other useful additives. Therefore, the present invention also concerns products containing a compound of formula (I) or a salt thereof and a compound of formula (II) or a salt thereof or stereoisomeric forms or mixtures thereof as a combination for simultaneous, separate or sequential use in antifungal applications. Such products may consists of a suitable package comprising containers with both active ingredients, preferably in formulated form. Such formulated forms in general have the same composition as described for the formulations containing both active ingredients.

Appropriate carriers and adjuvants for use in the compositions of the present invention may be solid or liquid and correspond to suitable substances known in the art of formulation, such as, for example natural or regenerated mineral substances, solvents, dispersants surfactants, wetting agents, adhesives, thickeners, binders, fertilizers or anti-freeze agents.

A particular mode of administering an active composition containing at least one of the active ingredients of formulae (I) and (II), is the administration to the aboveground parts of plants in particular to the leaves thereof (leaf-application). The number of applications and the administered doses are chosen in accordance with the biological and climatic conditions of life of the causative agent. The active ingredients though, can also be applied to the soil and get into the plants through the root system (systemic activity), in case the locus of the plants is sprayed with a liquid composition or if the compounds are added to the soil in a solid formulation e.g. in the form of a granulate (soil application). The compounds of formulae (I) and (II) can also be coated on seeds, in case the seed grains seed are drenched consecutively with a liquid composition of the active ingredients or if they are coated with a previously combined composition.

The compositions of the present invention are particularly useful in post-harvest treatment of fruits, especially citrus fruits. In the latter instance, the fruits will be sprayed with or dipped or drenched into a liquid formulation or the fruit may be coated with a waxy composition. The latter waxy composition conveniently is prepared by thoroughly mixing a suspension concentrate with a suitable wax. The formulations for spray, dip or drench applications may be prepared upon dilution of a suspension concentrate with an aqueous medium. Such suspension concentrate in most instances consists of the active ingredients, a dispersing or suspending agent (surfactant), a thickening agent, a small amount of organic solvent, a wetting agent, optionally some anti-freeze agent, and water.

The combinations of active ingredients of formulae (I) and (II) may in general be applied as compositions. The active ingredients of formula (I) and those of formula (II) can be applied either simultaneously, or consecutively, to the plants or the loci thereof, optionally in admixture with adjuvants conventionally employed in the art of formulation such as, for example, carriers, surfactants and other additives which may improve the application.

Apart from both the aforementioned active ingredients of formula (I) and (II), the compositions according to the present invention may further contain other active ingredients, e.g. other microbiocides, in particular fungicides, and also insecticides, acaricides, nematicides, herbicides, plant growth regulators and fertilizers. In particular, the compositions according to the present invention may contain further fungicides and preferably may contain the fungicide thiabendazole or a salt thereof. Thiabendazole is the generic name of the compound 2-(4-thiazolyl)-1H-benzimidazole, which compound may be represented by the formula

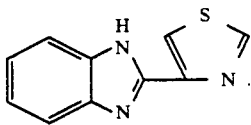

(III)

This compound, its synthesis as well as its antifungal properties are described in U.S. Pat. No. 3,017,415 incorporated herein by reference. The active ingredient thiabendazole may be present as such as or as salt form, either an acid addition salt, base addition salt or a metal complex as described hereinabove. In some instances, an additional synergistic effect between thiabendazole and the other active ingredients may be obtained. In the thiabendazole containing compositions according to the present invention, the weight ratio between thiabendazole and that active ingredient of formula (I) or (II) being the least present, will not exceed 50:1, and in particular will range from 20:1 to 1:1, more in particular from 5:1 to 1:1. The concentration of thiabendazole, taken as base equivalent, in the composition to be used directly to treat plants or their loci, or in particular to treat fruits, will be in the range of 200 to 10000 ppm, in particular from 400 to 8000 ppm or from 400 to 4000 ppm, more in particular from 750 to 1250 ppm. In the case of waxes for treating fruits, the concentration of thiabendazole will be in the range of 1000 to 10000 ppm, in particular of 1000 to 8000 or of 1000 to 4000 ppm, or 1500 to 2500 ppm.

The active ingredients of formula (I), (II) and (III) are used in unmodified form or, preferably, together with the adjuvants conventionally employed in the art of formulation. They are therefore formulated following art-known procedures to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomizing, dusting, scattering or pouring, are chosen in accordance with the intended objectives and the prevailing circumstances.

The formulations, i.e. the compositions, preparations or mixtures containing the active ingredients and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are aromatic hydrocarbons, preferably the fractions containing 8 to 12 carbon atoms, e.g. dimethylbenzene mixtures or substituted naphthalenes, phthalates such as dibutyl phthalate or dioctyl phthalate, aliphatic or alicyclic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated absorbent carriers are of the porous type, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Suitable surface-active compounds to be used in the compositions of the present invention are non-ionic, cationinic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, earth alkaline metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from cocoanut oil or tallow oil. In addition, there may also be mentioned fatty acid methyltaurin salts.

More frequently, however, so-called synthetic surfactants are used, especially fatty sulfonates, fatty sulfates, sulfonated benzimidazole derivatives or alkylarylsulfonates. The fatty sulfonates or sulfates are usually in the form of alkali metal salts, earth alkaline metal salts or unsubstituted or substituted ammonium salts and contain an alkyl radical having from 8 to 22 carbon atoms said alkyl also comprising radicals derived from acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutylnaphthalenesulfonic acid, or of a naphthalene-sulfonic acid/formaldehyde condensation product. Also suitable are corresponding phosphates. e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (alifatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopoly- propylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituent, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications: "McCutcheon's Detergents and Emulsifiers Annual", MC Publishing Corp., Ridgewood, N.J., 1981; N. Stache, "Tensid-Taschenbuch", 2nd Edition, C. Hanser Verlag, Munich & Vienna, 1981, M. and J. Ash, "Encyclopedia of Surfactants", Vol. I–III, Chemical Publishing Co., N.Y., 1980–81.

Particularly advantageous additives useful to improve the application and reduce the dose of the active ingredients, are the natural (animal or plant) or synthetic phospholipids of the cephalin or lecithin type such as, for example, phosphatidylethanolamine, phosphatidylserine, phosphatidylglycerine, lysolecithin, or cardiolipin. Such phospholipids may be obtained from animal or plant cells, in particular from brain-, heart- or liver tissue, egg yolks or soy beans. Appropriate such phospholipids are for instance, phosphatidylchlorin mixtures. Synthetic phospholipids are for instance, dioctanylphosphatidylchloline and dipalmitoylphosphatidylcholine.

In a further aspect of the present invention there is provided a method of combating fungi comprising treating plants or the loci thereof subsequently or simultaneously with a fungicidally effective amount of imazalil or a salt thereof and with propiconazole, a salt or stereoisomer or stereoisomeric mixture thereof, and optionally with further fungicides, in particular with thiabendazole or a salt thereof.

The synergistic activity of imazalil and propiconazole can be demonstrated in vitro but also in vivo, e.g. on oranges being inoculated with, for example, Geotrichum candidum and being dipped into a suitable liquid formulation containing both active ingredients.

The following examples are intended to illustrate and not to limit the scope of the present invention in all its aspects.

EXAMPLES

A) Composition Examples

Throughout all examples percentages are by weight.

| Example 1: Wettable powders | (a) | (b) | (c) |
|---|---|---|---|
| propiconazole | 10% | 25% | 0.25% |
| imazalil | 10% | 25% | 0.25% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7-8 moles of ethylene oxide) | — | 2% | 2% |
| highly dispersed silicic acid | 5% | 27% | 27% |
| kaolin | 67% | 10% | — |
| sodium chloride | — | — | 59.5% |

The active ingredient was thoroughly mixed with the adjuvants and the mixture was thoroughly ground in a suitable mill, affording wettable powders which could be diluted with water to give suspensions of the desired concentration.

| Example 2: Emulsifiable concentrates | (a) | (b) | (c) | (d) | (e) |
|---|---|---|---|---|---|
| propiconazole | 5% | 4% | 0.5% | 0.4% | — |
| imazalil | 5% | 2% | 0.5% | 0.2% | 2% |
| thiabendazole | — | 4% | — | 0.4% | 2% |
| octylphenol polyethylene glycol ether (4-5 moles of ethylene oxide) | 3% | 3% | 3% | 3% | 3% |
| calciumdodecylbenzenesulfonate | 3% | 3% | 3% | 3% | 3% |
| castor oil polyglycol ether (36 moles of ethylene oxide) | 4% | 4% | 4% | 4% | 4% |
| cyclohexanone | 30% | 30% | 10% | 10% | 20% |
| dimethylbenzene mixture | 50% | 50% | 79% | 79% | 66% |
| propiconazole | 5% | 2.5% | | | |
| imazalil | 5% | 2.5% | | | |
| calcium dodecylbenzenesulfonate | 5% | 8% | | | |
| castor oil polyethylene glycol ether (36 moles of ethylene oxide) | 5% | — | | | |
| tributylphenol polyethylene glycol ether (30 moles of ethylene oxide) | — | 12% | | | |
| cyclohexanone | — | 15% | | | |

| -continued | | | | | |
|---|---|---|---|---|---|
| Example 2: Emulsifiable concentrates | (a) | (b) | (c) | (d) | (e) |
| dimethylbenzene mixture | 80% | 60% | | | |

Emulsions of any required concentration could be obtained from these concentrate by dilution with water.

| Example 3: Dusts | (a) | (b) |
|---|---|---|
| propiconazole | 0.05% | 0.5% |
| imazalil | 0.05% | 0.5% |
| talcum | 99.9% | — |
| kaolin | — | 99% |

Usable dusts were obtained by mixing the active ingredient with the carriers, and grinding the mixture in a suitable mill.

| Example 4: Extruder granulates | (a) | (b) |
|---|---|---|
| propiconazole | 5% | 0.5% |
| imazalil | 5% | 0.5% |
| sodium lignosulfate | 2% | 2% |
| carboxymethylcellulose | 1% | 1% |
| kaolin | 87% | 96% |

The active ingredient was mixed and ground with the adjuvants, and the mixture was subsequently moistened with water. The mixture was extruded and dried in a stream of air;

| | (a) | (b) |
|---|---|---|
| propiconazole | 2.5% | 5% |
| imazalil | 2.5% | 5% |
| kaolin | 94% | — |
| highly dispersed silicic acid | 1% | — |
| attapulgite | — | 90% |

The active ingredient was dissolved in dichloromethane, the solution was sprayed onto the carrier, and the solvent was subsequently evaporated off in vacuo.

| Example 5: Coated granulate | |
|---|---|
| propiconazole | 1.5% |
| imazalil | 1.5% |
| polyethylene glycol (mol. wt. 200) | 2% |
| kaolin | 95% |

The finely ground active ingredient was uniformly applied, in a mixer, to the kaolin moistened with polyethylene glycol. Non-dusty coated granulates were obtained in this manner.

| Example 6: Suspension concentrate | (a) | (b) | (c) | (d) |
|---|---|---|---|---|
| propiconazole | 20% | 16% | 2.5% | 2% |
| imazalil | 20% | 8% | 2.5% | 1% |
| thiabendazole | 0% | 16% | 0% | 2% |
| ethylene glycol | 10% | 10% | 10% | 10% |
| nonylphenol polyethylene glycol ether (15 moles of ethylene oxide) | 6% | 6% | 1% | 1% |
| sodium lignosulfate | 10% | 10% | 5% | 5% |
| carboxymethylcellulose | 1% | 1% | 1% | 1% |
| 37% aqueous formaldehyde solution | 0.2% | 0.2% | 0.2% | 0.2% |
| silicone oil in the form of a 75% aqueous emulsion | 0.8% | 0.8% | 0.8% | 0.8% |
| water | 32% | 32% | 77% | 77% |

The finely ground active ingredient was intimately mixed with the adjuvants, giving a suspension concentrate from which suspension of any desired concentration could be obtained by dilution with water.

| | (a) | (b) |
|---|---|---|
| propiconazole | 5% | 2.5% |
| imazalil | 5% | 2.5% |
| ethylene glycol monoethyl ether | — | — |
| polyethylene glycol (MG 400) | 70% | — |
| N-methyl-2-pyrrolidone | 20% | — |
| expoxidised coconut oil | — | 1% |
| petroleum distillate (boiling range 160–190° C.) | — | 94% |

These solutions were suitable for application in the form of microdrops.

C. Biological examples

Example 7

In vitro activity of the compounds-alone or in mixtures-is tested in small Petri-dishes (diameter 55 mm) containing 7.2 ml potato dextrose agar. Stock solutions of the compounds are made in 50% ethanol in sterile flasks. Further dilutions are prepared with sterile distiled water. The test solutions (in a volume of 0.8 ml) are added to the PDA just before solidification of the medium (±) 50° C.). The final concentration of the test compounds are given in the table 1. *Penicillium italicum*, the causative agent of blue mould in citrus, is used as the test fungus. The inoculum is prepared by suspending an amount of conidia in sterile distiled water. Each Petri-dish is inoculated in the center of the dish by means of a needle previously dipped in the spore suspension. The activity of the compounds is evaluated by measuring the diameter of fungal growth after 5 days at 20° C.±2° C. Relative Activities were calculated by taking no fungal growth (diameter is 0 mm) as 100%. The expected activities E were calculated by using the so-called formula of Colby: (Colby, S. R. Weeds 1967, 15:20–22)

$$E = X + Y - \frac{X \cdot Y}{100}$$

where X and Y express the relative activities obtained for each of the active ingredients when tested above. A synergistic effect can be acknowledged if the found activity exceeds calculated activity. The following Table lists the relative activities and the calculated activities for a number of mixtures of the compounds of formula (I) and (II) or (III).

TABLE 1

In the following table the test concentrations are given in ppm a.i.

| | imazalil (I) | propiconazole (II) | growth (in mm) | calculated activity | relative activity |
|---|---|---|---|---|---|
| Untreated | — | — | 17 | — | — |
| 1 | 1 | — | 0 | — | 100 |
| | 0.3 | — | 0 | — | 100 |
| | 0.1 | — | 1 | — | 94 |
| | 0.03 | — | 5 | — | 71 |
| | 0.01 | — | 15 | — | 12 |

TABLE 1-continued

In the following table the test concentrations are given in ppm a.i.

| | imazalil (I) | propico-nazole (II) | growth (in mm) | calculated activity | relative activity |
|---|---|---|---|---|---|
| 2 | — | 1 | 0 | — | 100 |
| | — | 0.3 | 1 | — | 94 |
| | — | 0.1 | 4 | — | 76 |
| | — | 0.03 | 8 | — | 53 |
| | — | 0.01 | 13 | — | 24 |
| 3 | 1 | 1 | 0 | 100 | 100 |
| | 0.3 | 0.3 | 0 | 100 | 100 |
| | 0.1 | 0.1 | 0 | 99 | 100 |
| | 0.03 | 0.03 | 0 | 86 | 100 |
| | 0.01 | 0.01 | 6 | 33 | 65 |

We claim:

1. An antifungal composition comprising a carrier and, as the active ingredients, a fungicidally effective quantity of a mixture of (I) imazalil, or a fungicidally acceptable salt thereof, and (II) propiconazole, or a fungicidally acceptable salt, a stereoisomer, or stereoisomeric mixture thereof, wherein the active ingredients (I) and (II) are employed in proportions wherein the ratio by weight of (I) and (II) is within the range of from 1:50 to 50:1, and wherein said proportions produce a synergistic antifungal effect.

2. A composition according to claim 1 wherein the ratio by weight between both active ingredients is from 10:1 to 1:10.

3. A composition according to claim 1 wherein the ratio by weight between both active ingredients is from 5:1 to 1:5.

4. A composition according to claim 1 comprising form 100 to 5000 ppm of imazalil base equivalent and from 200 to 1000 ppm of propiconazole base equivalent.

5. A composition according to claim 1, containing as further active ingredient thiabendazole.

6. A composition according to claim 5 wherein the weight ratio between thiabendazole and the other active ingredient being the least present does not exceed 50.

7. A composition according to claim 4 also containing form 200 to 10000 ppm of thiabendazole.

8. A composition containing the combination of a fungicidally effective quantity of (I) imazalil or a fungicidally acceptable salt thereof and (II) propiconazole, a fungicidally acceptable salt, a stereoisomer, or stereoisomeric mixture thereof as a combination for simultaneous, separate or sequential use in antifungal applications, wherein said ingredients (I) and (II) are employed in proportions wherein the ratio by weight of (I) and (II) is within the range of from 1:50 to 50:1, and wherein said proportions produce a synergistic antifungal effect.

9. A method of combating fungi comprising treating plants or the loci thereof separately or simultaneously with a fungicidally effective amount of (I) imazalil or a fungicidally effective salt thereof and (II) propiconazole, a fungicidally effective salt or stereoisomer or stereoisomeric mixture thereof, said ingredients (I) and (II) being employed in proportions wherein the ratio by weight of (I) and (II) is within the range of from 1:50 to 50:1, and wherein said proportions produce a synergistic antifungal effect.

10. A method according to claim 9 wherein the plants or loci thereof are also treated with thiabendazole or a salt thereof.

11. A method of combating fungi comprising treating plants or the loci thereof with an effective amount of a composition as claimed in claim 1.

* * * * *

UNITED STATES PATENT AND TRADEMARK OFFICE
CERTIFICATE OF CORRECTION

PATENT NO. : 5,013,746

DATED : May 7, 1991

INVENTOR(S) : Jozef F. E. Van Gestel, et al.

It is certified that error appears in the above-identified patent and that said Letters Patent is hereby corrected as shown below:

The title page should be deleted to appear as per attached title page.

Signed and Sealed this

Twenty-third Day of July, 1991

*Attest:*

HARRY F. MANBECK, JR.

*Attesting Officer*      *Commissioner of Patents and Trademarks*

United States Patent [19]

Van Gestel et al.

[11] Patent Number: 5,013,746
[45] Date of Patent: May 7, 1991

[54] IMAZALIL CONTAINING SYNERGISTIC COMPOSITIONS

[75] Inventors: Jozef F. E. Van Gestel, Vosselaar; Jan R. Nys, Antwerp; Paul F. M. Ruelens, Herk-de-Stad, all of Belgium

[73] Assignee: Janssen Pharmaceutica N.V., Beerse, Belgium

[21] Appl. No.: 335,023

[22] Filed: Apr. 7, 1989

Related U.S. Application Data

[63] Continuation-in-part of Ser. No. 284,761, Dec. 12, 1988, abandoned, which is a continuation of Ser. No. 179,451, Apr. 8, 1988, abandoned.

[51] Int. Cl.$^5$ ............... A01N 43/50; A01N 43/64; A01N 43/78
[52] U.S. Cl. ............... 514/365; 514/383; 514/399
[58] Field of Search ............... 514/365, 383, 399

[56] References Cited

U.S. PATENT DOCUMENTS

| | | | |
|---|---|---|---|
| 3,017,415 | 1/1962 | Sarett et al. | 260/302 |
| 3,658,813 | 4/1972 | Godefroi et al. | 260/240 K |
| 4,079,062 | 3/1978 | Van Reet et al. | 260/308 R |
| 4,507,140 | 3/1985 | Sugavanam | 71/76 |
| 4,636,247 | 1/1987 | Clough et al. | 71/92 |

FOREIGN PATENT DOCUMENTS

| | | | |
|---|---|---|---|
| 0209234 | 1/1987 | European Pat. Off. | 548/341 |
| 2823818 | 12/1979 | Fed. Rep. of Germany | 548/127 |
| 2922292 | 2/1980 | Fed. Rep. of Germany | 514/184 |
| 2916853 | 11/1980 | Fed. Rep. of Germany | 548/262 |

OTHER PUBLICATIONS

Hide et al., Control of Potato Diseases with Fungicides Applied to Seed Tubers, Tests of Agorchemicals and Cultivars 8 (1987), Ann. Appl. Biol. 110 (supplement), pp. 72–73.

Hide et al., Chem. Abst. 107:54035m (1987).

*Primary Examiner*—Dale R. Ore
*Attorney, Agent, or Firm*—Charles J. Metz

[57] ABSTRACT

Synergistic antifungal compositions containing imazalil and propiconazole. Methods of treating plants comprising the administration of imazalil and propiconazole.

11 Claims, No Drawings